United States Patent [19]

Rossey et al.

[11] Patent Number: 4,656,278

[45] Date of Patent: Apr. 7, 1987

[54] ISOQUINOLINE DERIVATIVES AND THEIR PREPARATION

[75] Inventors: Guy Rossey, Montigny-le-Bretonneux; Didier Legroux, Domont, both of France

[73] Assignee: Synthelabo, Paris, France

[21] Appl. No.: 733,928

[22] Filed: May 14, 1985

[30] Foreign Application Priority Data

May 15, 1984 [FR] France ................................ 84 07465

[51] Int. Cl.$^4$ ............................................ C07D 217/24
[52] U.S. Cl. ..................................... 546/140; 546/141
[58] Field of Search ............................... 546/141, 140

[56] References Cited

U.S. PATENT DOCUMENTS

| | | | |
|---|---|---|---|
| 3,379,730 | 4/1968 | Mathison | 546/140 |
| 4,375,471 | 3/1983 | Effland et al. | 546/141 |
| 4,438,121 | 3/1984 | Obitz | 546/141 |

OTHER PUBLICATIONS

Noller, *Chemistry of Organic Compounds;* Sec. Ed., 1957, W. B. Saunders Co., Philadelphia, pp. 873–875.

*Primary Examiner*—Richard L. Raymond
*Attorney, Agent, or Firm*—Wegner & Bretschneider

[57] ABSTRACT

Isoquinoline derivatives of the formula (I)

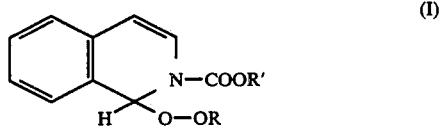

(I)

in which R is a group selected from t-butyl and groups of the formula

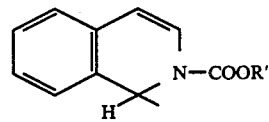

and R' is selected from methyl and ethyl, are useful in the preparation of 1(2H)-isoquinolone.

4 Claims, No Drawings

ISOQUINOLINE DERIVATIVES AND THEIR PREPARATION

The present invention relates to isoquinoline derivatives, their preparation and their applications.

The isoquinoline derivatives of the invention are of the formula

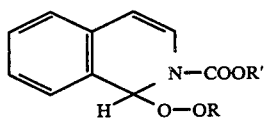
(I)

in which R is a group selected from t-butyl and groups of the formula

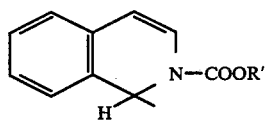

and R' is selected from methyl and ethyl.

According to the invention the isoquinoline derivatives (I) can be prepared from isoquinoline by reaction with tert-butyl hydroperoxide or hydrogen peroxide, in a solvent such as methylene chloride or alcohols (methanol, ethanol or propanol), in the presence of a base, such as triethylamine or sodium or potassium bicarbonate, and methyl or ethyl chloroformate, suitably at a temperature of 0° C. to 30° C.

The isoquinoline derivative of the invention can be used to prepare 1(2H)-isoquinolone, a compound which is useful for the synthesis of the compound 7 described in French Pat. No. 81 10428 (U.S. Pat. No. 4,438,121).

The conversion of isoquinoline derivatives of formula (I) to 1(2H)-isoquinolone can be carried out in a basic medium in a solvent, such as aprotic or protic polar solvents, for example by the treatment of an isoquinoline derivative of formula (I) with 50% strength sodium hydroxide in dimethyl sulphoxide (DMSO) or with a sodium methoxide/methanol mixture.

The following Examples illustrate the invention. The structures of the compounds were confirmed by analyses and IR and NMR spectra.

EXAMPLE 1

Methyl (1-(1,1-dimethylethyl)dioxy-2(1H)-isoquinolinecarboxylate

Into a 100-ml round-bottomed flask, placed in an ice-bath, equipped with a constant-pressure dropping funnel and a magnetic stirrer, are added 6.5 g of isoquinoline, 25 ml of CH$_2$Cl$_2$, 7.5 g of Et$_3$N and 6.4 g of Me$_3$COOH. 5.8 ml of ClCOOCH$_3$ are then added dropwise (slightly exothermic) over 15 min and the reaction mixture is stirred for 2 hours.

100 ml of water are then added, the organic phase is separated off, and washed with 20 ml of water. It is separated, dried over Na$_2$SO$_4$ and then concentrated. A colorless residue is obtained which solidifies when cold.

After recrystallization from an isopropanol/water mixture the resulting compound melts at 72.7°-73° C.

EXAMPLE 2

Bis-(methyl 1-oxy-2(1H)-isoquinolinecarboxylate).

Into a 100-ml round-bottomed flask maintained at −10° C. are added 12.9 g of isoquinoline, 50 ml of methylene chloride, 12.6 g of sodium bicarbonate and 10 ml of H$_2$O$_2$. 11.6 ml of ClCOOCH$_3$ are added dropwise over 15 minutes, and then allowed to react for 2 hours while the temperature returns to ambient temperature. 50 ml of water and 300 ml of diisopropyl ether are added to the reaction mixture; the resulting white solid is filtered off and then dried under vacuum at 25° C. overnight.

The compound obtained melts at 175° C.

EXAMPLE 3

1(2H)-Isoquinolone

Into a 250 ml round-bottomed flask fitted with a condenser and magnetic stirring are added 14.83 g of the product obtained in Example 1, 100 ml of MeOH, and then 14 ml of a MeO$^-$Na$^+$/MeOH mixture of 29% strength.

The temperature is raised to reflux (bath at 93° C.) for 65 min.

The reaction mixture yellows slightly and then becomes opaque. It is allowed to cool, 20 ml of H$_2$O are added and the solution is concentrated, then 100 ml of H$_2$O are added. The solid formed is filtered off and suspended in 30 ml of t-BuOMe, and the compound is filtered off and dried in air and then under vacuum. The compound obtained melts at 212° C.

EXAMPLE 4

1(2H)-Isoquinolone

Into a 100-ml round-bottomed flask are added 2 g of the compound obtained in Example 2, 10 ml of DMSO, 8 g of NaHCO$_3$ and the reaction mixture is heated at 110° C. for 3 hours. 80 ml of water are then added, the isoquinolone is allowed to recrystallize and is filtered off and dried. It is purified by being suspended in t-BuOMe and being filtered as in Example 3. The compound obtained melts at 212° C.

We claim:

1. Isoquinoline derivatives of the formula (I)

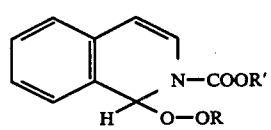
(I)

in which R is a group selected from t-butyl and groups of the formula

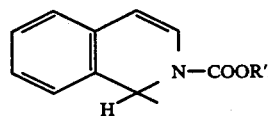

and R' is selected from methyl and ethyl.

2. Methyl 1-(1,1-dimethylethyl)dioxy-2(1H) isoquinoline carboxylate.

3. Bis-(methyl 1-oxy-2(1H)-isoquinoline carboxylate).

4. A process for the preparation of 1(2H)-isoquinolone from compounds of formula (I), as defined in claim 1, comprising:
    treating said isoquinoline derivative of formula (I) with a base in a solvent.